United States Patent [19]

Chen et al.

[11] 4,420,563

[45] Dec. 13, 1983

[54] PROCESS FOR THE PRODUCTION OF OSMOTOLERANT YEAST

[75] Inventors: Shao L. Chen; Feliks Gutmanis, both of Milwaukee, Wis.

[73] Assignee: Universal Foods Corporation, Milwaukee, Wis.

[21] Appl. No.: 389,321

[22] Filed: Jun. 17, 1982

Related U.S. Application Data

[63] Continuation of Ser. No. 140,262, Apr. 14, 1980, abandoned.

[51] Int. Cl.$^3$ ............................................. C12N 1/36
[52] U.S. Cl. .................................. 435/245; 435/256; 426/60
[58] Field of Search ................... 426/60, 62; 435/256, 435/942, 245

[56] References Cited

U.S. PATENT DOCUMENTS

| | | | |
|---|---|---|---|
| 1,727,847 | 9/1929 | White | 435/245 |
| 1,745,693 | 2/1930 | Hixson et al. | 435/256 |
| 2,947,668 | 8/1960 | Kuestler et al. | 426/62 |
| 3,617,306 | 11/1971 | Pomper et al. | 435/256 |

*Primary Examiner*—Hiram H. Bernstein
*Attorney, Agent, or Firm*—Neuman, Williams, Anderson & Olson

[57] ABSTRACT

Osmotolerant yeasts having high activity in sweet doughs are obtained in high yield by incremental addition or feeding of salts such as NaCl, KCl, $CaCl_2$, $MgCl_2$, $Na_2SO_4$, $MgSO_4$, and $K_2SO_4$ in the latter propagative stages of yeast production.

14 Claims, No Drawings

PROCESS FOR THE PRODUCTION OF OSMOTOLERANT YEAST

This is a continuation of application Ser. No. 140,262 filed Apr. 14, 1980 now abandoned.

FIELD OF THE INVENTION

The field of the instant invention is the manufacture of baker's compressed yeast and active dry yeast having an enhanced tolerance to the high osmotic pressure in the dough systems, and hence improved leavening activity, particularly in sweet doughs of high sugar content.

BRIEF DESCRIPTION OF THE PRIOR ART

A typical commercial operation for producing yeast is described in Reed & Peppler, *Yeast Technology*, pages 79-80 (1973). That process starts in the laboratory, where Pasteur flasks containing a rich medium (malt extract or malt extract molasses blend) are inoculated from slants of the pure yeast culture. The contents of the Pasteur flasks, after typically 2-3 days incubation, is then inoculated into small pure culture fermentors, usually a series of three pure culture fermentors with capacities of, e.g., 20 gal., 100 gal. and 1000 gal. The yeast is grown in these fermentors in a sterile medium rich is growth factors. There is no incremental feeding of nutrients and/or molasses in this growth stage and little aeration. The air used in customarily sterilized. The last pure culture stage has been designated the (F1) stage.

The pure culture fermentor stages are followed by one or more incrementally fed stages (F2, F3, etc.). A portion of the fermentor contents of the (F1) stage is pumped into a larger tank for the first incrementally fed stage (F2). From this point on in the yeast propagation system, aeration is vigorous and molasses and other nutrients are fed incrementally. After completion of each of these incrementally fed stages of fermentation, the yeast is separated from the bulk of the fermentor liquid (beer) by centrifuging, producing a stock of yeast for the next stage. The fermentor contents of a completed incrementally fed stage is usually divided into several parts for pitching of the next stage of fermentation. After the final incrementally fed stage of fermentation, the yeast is removed from the fermentor beer by centrifugation and washed one or more times by resuspending in water to prepare the yeast for pressing and further processing to produce a product for commerce.

Incremental feeding, as used above, refers to the practice of adding the molasses and other nutrients to the fermentor liquid-yeast mixture at such a rate that molasses is consumed by the yeast at the same rate it is added. This practice is also known in the art as the "Zulauf" technique.

It is well-known in the art of yeast propagation that generally, high osmotic pressure occasioned by high concentrations of salts in a yeast-growing medium substantially retards the rate of growth of yeast cells, resulting in low yields. It is also known that in general, yeasts with a low sensitivity to osmotic pressure, i.e., yeasts defined as being "osmotolerant", possess superior leavening or gas-producing properties in dough systems, particularly in sweet doughs, i.e., those which contain a high amount of solubles such as sugar. Hence, to produce a yeast with superior osmotolerance, it is necessary to use an inherently low-yielding process. It is therefore difficult to economically produce an osmotolerant yeast.

It is further well-known in the art that non-nutritive ionic salts, generally halides, sulfates, or carbonates of elements from Groups 1a and 2a of the Periodic Chart, may significantly increase the osmotic pressures in yeast propagation media and in doughs.

An early attempt to produce an osmotolerant yeast with superior leavening properties is represented by John R. White, U.S. Pat. No. 1,727,847. In that process, yeast is grown in a series of stages where from about $\frac{1}{2}\%$ to about 5% sodium chloride is added to each successive stage to impart osmotolerance to the yeast. A later attempt is represented by U.S. Pat. No. 3,617,306, where the yeast is grown in a series of stages, but the salt content is kept to below 0.2% in all fermentation stages except the last, where the salt content is raised, preferably to between 0.3% and 1%.

In U.S. Pat. No. 3,617,306 it is stated at Col. 3, lines 73-75, that addition of a non-nutritive salt in the final propagation stage may either be incremental during the propagation stage or all at once at the start of the propagation stage. In Example VI, a comparison of yeasts prepared by incremental addition and addition at the beginning of a stage at 0.34% NaCl concentration was made, and no difference in activity of the yeasts was found.

The primary disadvantage of the method of U.S. Pat. No. 1,727,847, is its inherently low yield. Whereas the method of U.S. Pat. No. 3,617,306 is a considerable improvement over U.S. Pat. No. 1,727,847, it would nevertheless be desirable to find a method yielding even better results.

Yeast doughs are classified herein according to relative amounts of sugars present in them, ranging from "lean" doughs, with no added sugar, through "straight" doughs, with a sugar content of 2 to 4% by weight, to "sweet" doughs, with a sugar content of 20 to 30% by weight. In general, the osmotic pressures in sweet doughs are higher, due to increased sugar content.

BRIEF DESCRIPTION OF THE INVENTION

This invention relates to a method of producing an osmotolerant yeast in stages by the addition of non-nutritive salt in an incremental fashion during each successive incrementally fed stage of yeast propagation. Commercially available molasses usually contains enough salts so that a full effect is obtained without the need to add additional salts to any but the final incrementally fed stage of fermentation. The method produces an osmotolerant yeast in high yield with superior leavening properties, as contrasted with an osmotolerant yeast produced by adding a non-nitritive salt all at once at the outset of the final yeast propagation stage as shown in the prior art.

In a normal production run of conventional commercial yeast, it is desirable to use a molasses with a sufficient content of salts such that during the aerobic stages corresponding to the (F1), (F2) and (F3) stages mentioned by the Reed & Peppler reference, the total ionic concentration of Na, K, Mg, Cl and $SO_4$ ions in the spent beer is between 1% and 2% on a w/v basis. If necessary, sufficient amounts of $MgSO_4$, KCl and $CaCl_2$ may be added incrementally during these stages to produce the requisite ionic concentrations. In the final incrementally fed stage of fermentation for non-osmotolerant yeast, it is desirable to obtain a total ionic concentration of at least 2.5%. If for any reason, the salt content in the fermentor beer at the end of the final incrementally fed stage of fermentation is less than about 2.5%, the resulting yeast produced will have less omotolerance than is desirable in commerce.

To produce an osmotolerant yeast in accordance with the method of the present invention, ingredients and conditions follow those outlined for a normal production run of conventional commercial yeast except that in the final incrementally fed stage of fermentation, an additional amount of non-nitritive salt is incrementally added. Exemplary of such non-nutritive salts are $MgSO_4$, $K_2SO_4$, KCl, $CaCl_2$ and NaCl. The additional salt is added to the extent of about 0.3% to about 5% on a w/v basis. The preferred amount differs for different salts. For NaCl and $CaCl_2$, the preferred amount is from about 0.3% to about 1.25%.

The following Example demonstrates the production of a non-osmotolerant yeast:

EXAMPLE 1

(A) Pure Culture I (R1)

To a 15 gallon fermenter were added the following ingredients:
Malt—9 lbs.
Molasses—18 lbs.
Defoamer—100 ml.
Water—11-13 gals.

The ingredients were mixed and brought to a temperature of 82° F. The pH was adjusted to between 4.0 and 4.5 with phosphoric acid, and two culture flasks of yeast, containing 3000 cc growth medium and about 2.5 g of yeast were added. The yeast was allowed to ferment for 16-24 hours. The yeast strain used was "F-31", a strain of baker's yeast (*Saccharomyces cerevisiae*) produced by Universal Foods Corporation, Milwaukee, Wisconsin. Although this yeast is not available in a public culture collection, it is a typical baker's yeast suitable for use as a compressed yeast. Similar results are predicted for other baker's yeast strains that are suitable for use as compressed yeasts.

(B) Pure Culture II Stage (R2)

To a 160 gallon fermentor were added the entire contents of the Pure Culture I stage mixture, with 130 gals. water, 200 lbs. of molasses and 1 lb. of defoamer. The pH was adjusted to between 4.0 and 4.5 with phosphoric acid, and the temperature was maintained at 82° F. The yeast was allowed to ferment for 12-20 hours under mildly aerobic conditions.

(C) Pure Culture III Stage (F1)

To a 5,000 gallon fermentor were added the entire contents from the Pure Culture II stage along with the following ingredients.
Water—4000-4400 gals.
Molasses—4,500 lbs.
Ammonia—40 lbs.
Phosphoric acid—50 lbs.
Defoamer—20 lbs.

The temperature was maintained at 82° F. and the pH was kept between 4.0 and 4.5 by addition of sulfuric acid as required. The yeast was allowed to ferment for 15-20 hours. A portion of the spent beer was retained for analysis.

(D) Incremental Feed Stage I (F2)

To a 500 gallon fermentor were added:
Water—200 gals.
Epsom salts—2 lbs.
Potassium Chloride—1 lb.
Calcium Sulfate—0.5 lb.
Zinc Sulfate—0.02 lb.

and 90 gallons of yeast slurry of Pure Culture III Stage (F1). Phosphoric acid (6 lbs.) and sulfuric acid (6.5 lbs.), stored in separate vessels, were added over a period of 5-6 hours. Ammonia (approximately 35 lbs.) was added as required for maintaining pH at 4.0 to 5.0. Molasses (310 lbs.) was fed incrementally to the fermentor over a period of 20 hours at 30° C. The yeast-beer mixture was centrifuged to obtain 50 gals. of yeast slurry. A portion of the spent beer was retained for analysis.

(E) Incremental Feed Stage II (F3)

50 lbs. of yeast obtained from the Incremental Feed Stage I (F2) was used to pitch the Incremental Feed Stage II (F3) fermentor (500 gals.), which contains the following ingredients:
Water—350 gals.
Magnesium Sulfate—2.5 lbs.
KCl—1 lb.
Calcium Sulfate—0.5 lbs. Phosphoric acid (4.8 lbs.) and sulfuric acid (3 lbs.), stored in separate vessels, were fed over a period of 5-6 hours. Ammonia (about 30 lbs.) was added as required for maintaining pH at 4.0 to 5.0. Molasses (360 lbs.) was fed incrementally to the fermentor over a period of 12 hours at 30° C. The resultant yeast-beer mixture was centrifuged to obtain 70 gals. of yeast slurry. A portion of the spent beer was retained for analysis.

(F) Incremental Feed Stage III (F4)

To a 500 gallon fermentor were added 75.5 lbs. of yeast from the Incremental Feed Stage II (F3), together with the following ingredients:
Water—370 gals.
Magnesium sulfate—2.5 lbs.
KCl—1 lb.
Calcium sulfate—0.5 lb.
Phosphoric acid (3 lbs.) and sulfuric acid (3 lbs.), stored in separate vessels, were added to the fermentor over a period of 5-6 hours. Ammonia (about 30 lbs.) was added as required for maintaining pH at 4.0 to 5.5. Molasses (360 lbs.) was fed incrementally to the fermentor over a period of 12 hours at 30° C. The yeast was centrifuged and pressed in a conventional fashion to obtain a compressed cake. A portion of the spent beer was retained for analysis. The yield was about 87%. The fermentation activity of this product is given in Examples, 4, 5 and 6.

The following Example demonstrates the presence of ionic species in the above-described regular yeast fermentation process:

EXAMPLE 2

The spent beer from the (F1), (F2), (F3) and (F4) stages was analyzed for various cationic and anionic species. The freezing points of the spent beers were likewise found and equivalent NaCl concentrations from standard brine freezing tables were determined. The results are reported in Table I, following.

TABLE I

| | Salt Concentration in Spent Beer Regular Fermentation Process | | | | | | | |
|---|---|---|---|---|---|---|---|---|
| | Cation, % | | | Anion, % | | Total % Anion & Cation | Freeze pt. dep (°C.) | NaCl equiv (%) |
| Fermentation Stage | Na | K | Mg | Cl | $SO_4$ | | | |
| 1. Pure Culture Stage 3 (F1) | .156 | .475 | .002 | .21 | .49 | 1.333 | −2.26 | 3.90 |
| 2. Incremental Feed Stage 1 (F2) | .156 | .550 | .007 | .25 | .98 | 1.943 | −1.32 | 2.32 |
| 3. Incremental Feed Stage 2 (F3) | .131 | .488 | .008 | .21 | .97 | 1.807 | −1.22 | 2.13 |
| 4. Incremental Feed Stage 3 (F4) | .194 | .750 | .012 | .28 | 1.31 | 2.545 | −1.50 | 2.60 |

The following Example demonstrates the production of osmotolerant yeast according to the present invention:

EXAMPLE 3

Example (1) was repeated, except that 22 lbs. of NaCl were added to the molasses holding tank at the beginning of the final incrementally fed stage (F4). The molasses containing the added salt was then fed to the final incrementally fed stage in the way that molasses alone is usually added. The total NaCl added in this final fermentation stage was thus 0.63% on a w/v basis (based on final volume). An osmotolerant yeast (83% yield) with superior leavening properties was obtained. The results of the fermentation tests with this yeast are described in Examples 4, 5 and 6.

EXAMPLE 4

A flour premix was prepared by mixing the following ingredients:
Flour—1,000 g.
Sugar—40 g.
Salt—20 g.
Non-Fat Dry Milk—40 g.
Vegetable Shortening—30 g.

From the flour premix were prepared two samples of sweet dough with the following composition:
Flour Premix—455 g.
Sugar—65 g.
Compressed Yeast—16 g.
Water (70° F.)—230 ml.

In one sample, the compressed yeast was the non-osmotolerant yeast prepared according to Example 1; in the other sample was used the osmotolerant yeast from Example 3. After proper mixture and dough formation in a dough-mixer, 155 g. of each sample were placed in an "SJA Fermentograph" (manufactured by A. B. Nassjo Metallverkstad, Nassjo, Sweden), set at 38° C. The amount of carbon dioxide produced in two hours by each sample was recorded. Average fermentation activity of non-osmotolerant yeast was 500-520 ml. $CO_2$. Average fermentation activity of osmotolerant yeast was 730-740 ml.

EXAMPLE 5

Two samples of straight dough were prepared from the following ingredients:
Flour Premix (from example 4)—455 g.
Compressed Yeast—8 g.
Water (70° F.)—270 ml.

In one sample, the yeast used was the non-osmotolerant yeast obtained according to Example 1; in the other sample, the yeast used was the osmotolerant yeast from Example 3. The dough samples were prepared and developed in a commercial dough mixer. 250 g. of each dough were placed in "SJA Fermentographs" at 38° C., and the amount of $CO_2$ produced in 60 minutes was measured. Average fermentation activity of the non-osmotolerant yeast was about 460-480 ml.; average fermentation activity of the osmotolerant yeast was about 590-600 ml.

EXAMPLE 6

Two samples of lean dough were prepared from the following ingredients:
Flour—400 g.
Salt—8 g.
Shortening—12 g.
Compressed Yeast—8 g.
Water (70° F.)—270 ml.

In one sample, the yeast used was the non-osmotolerant yeast obtained according to Example 1; in the other sample, the yeast used was the osmotolerant yeast from Example 3. The dough samples were prepared and developed in a commercial dough mixer. 225 g. of each dough were placed in "SJA Fermentographs" at 38° C., and the amount of $CO_2$ produced in 90 minutes was measured. Average fermentation activity of the non-osmotolerant yeast was about 680-700 ml.; average fermentation activity of the osmotolerant yeast was about 730-750 ml.

EXAMPLE 7

Example (1) was five times repeated, except that 11 lbs. of NaCl were added to the molasses holding tank at the beginning of the final incrementally fed stage (F4). The salt-containing molasses was fed to the final incrementally fed stage in the usual manner. The total NaCl added in this final fermentation stage was thus 0.33% on a w/v basis. An osmotolerant yeast with superior leavening activity in the sweet dough system was obtained. The average fermentation activity of the yeasts produced in this manner was 749 ml. $CO_2$, as compared to an average of 582 ml. $CO_2$ for the controls.

The following examples demonstrate the superiority of osmotolerant yeast produced by incremental feeding of the non-nutritive salt during the final stage of propagation over osmotolerant yeast produced by addition of non-nutritive salts directly to the fermentor at the outset of the final propagation stage:

EXAMPLES 8-18

In this series of examples, the steps of Example 3 were repeated, but on a laboratory scale. Various concentrations of NaCl, or KCl and $CaCl_2$ in lieu of the specific w/v percentage of NaCl employed in Example 3 were used. Example 3 was also repeated on a laboratory scale, but modified to the extent that rather than being added to the molasses wort, and fed incrementally to the fermentor, the non-nutritive salts were added directly to the fermentor at the outset (Examples 10, 11, 14, 15 and 17). Yeasts prepared according to Example 1 were used as controls. The final yields of yeast as a percentage of molasses used were calculated, and the fermentation activities of the yeasts were measured in straight, lean, and sweet doughs for 60 to 120 minutes in an "SJA Fermentograph".

The following results were obtained:

TABLE II

| EXAMPLE | Salt | Method | Yield % | Straight Dough | Lean Dough | Sweet Dough |
|---------|------|--------|---------|----------------|------------|-------------|
| 8 | 2.5% NaCl | Incremental | 76.5 | 521 | 721 | 612 |
| 9 | 2.5% NaCl | Incremental | 75.0 | 537 | 732 | 623 |
| 10 | 2.5% NaCl | To Fermentor | 57.2 | 521 | 754 | 620 |
| 11 | 2.5% NaCl | To Fermentor | 54.2 | 518 | 780 | 559 |
| 12 | 2.5% KCl | Incremental | 80.8 | 515 | 721 | 605 |
| 13 | 2.5% KCl | Incremental | 79.3 | 515 | 673 | 594 |
| 14 | 2.5% KCl | To Fermentor | 63.8 | 532 | 754 | 558 |
| 15 | 2.5% KCl | To Fermentor | 64.0 | 512 | 761 | 579 |
| 16 | 1.25% $CaCl_2$ | Incremental | 87.8 | 512 | 706 | 572 |
| 17 | 1.25% $CaCl_2$ | To Fermentor | 80.2 | 496 | 732 | 503 |
| 18 | None | Control (Average of 9 runs) | 87.0 | 480 | 690 | 515 |

As can be readily seen from the above (Table II), the osmotolerant yeasts perform better than the control yeasts in the "SJA Fermentograph" tests. There is a yield reduction (except for 1.25% $CaCl_2$) when a non-nutritive salt is used in the last stage of yeast propagation. However, the reduction in yield is significantly and unexpectedly greater where the non-nutritive salts are added to the fermentation vat at the outset of the propagation stage, rather than incrementally during the propagation stage.

The following examples more particularly demonstrate the relationship between yield and salt concentration were the addition is incremental:

EXAMPLES 19–28

Example 3 was repeated on a laboratory scale using various non-nutritive salts at various concentrations. The feed method in all cases was incremental. The final yields of yeast as a percentage of molasses used were calculated, and the fermentation activities of the yeasts were measured in straight, lean, and sweet doughs for 60 to 120 minutes in an "SJA Fermentograph." Yeast prepared according to Example 1 was used as a control. The following data were obtained:

TABLE III

| EXAMPLE | Salt | Yield % | Straight Dough | Lean Dough | Sweet Dough |
|---------|------|---------|----------------|------------|-------------|
| 19 | 5% NaCl | 66.5 | 549 | 741 | 652 |
| 20* | 2.5% NaCl | 75.8 | 529 | 728 | 620 |
| 21* | 1.25% NaCl | 79.7 | 518 | 721 | 634 |
| 22* | .625% NaCl | 83.1 | 501 | 699 | 598 |
| 23 | 5% KCl | 80.8 | 515 | 721 | 605 |
| 24* | 2.5% KCl | 80.1 | 515 | 699 | 601 |
| 25 | 1.25% $CaCl_2$ | 87.8 | 512 | 706 | 572 |
| 26 | .625% $CaCl_2$ | 85.2 | 512 | 680 | 558 |
| 27 | .625% $K_2SO_4$** | 88.3 | 473 | 673 | 426 |
| 28 | None - Control (Average of 9 runs) | 86.4 | 476 | 673 | 496 |

*Average of 2 runs.
**The yeast of Example 26 was superior to its side-by-side control in all doughs by about 15 ml. of $CO_2$.

As can be seen from the above, a significant improvement in fermentation activity of yeast products was achieved under these conditions with NaCl additions as low as 0.6%. Above 1.25%, the sacrifice in yeast yield may be unacceptable. $CaCl_2$, as well, shows excellent improvement in leavening activity with a minimum sacrifice in yield at 0.625% and at 1.25%. KCl shows excellent results at both 2.5% and at 5%.

The following examples demonstrate the storage stability of compressed yeast made according to the present process.

EXAMPLES 29–34

Compressed yeasts were made according to the method of Example 3. They were tested in straight, lean, and sweet dough systems in an "SJA Fermentograph" for 60–120 minutes immediately after production, and after 2 weeks and 4 weeks of storage at 35°–40° F. The following results were obtained:

TABLE IV

| | | Fermentation Activities During Storage, ml. ($CO_2$) | | | | | | | | |
|---|---|---|---|---|---|---|---|---|---|---|
| | | Straight Dough | | | Lean Dough | | | Sweet Dough | | |
| EXAMPLE | Treatment | 0 wk | 2 wk | 4 wk | 0 wk | 2 wk | 4 wk | 0 wk | 2 wk | 4 wk |
| 29 | 1.25% NaCl | 521 | 470 | 403 | 710 | 650 | 598 | 641 | 503 | 433 |
| 30 | Control | 493 | 456 | 395 | 654 | 617 | 546 | 594 | 445 | 379 |
| 31 | 2.50% NaCl | 538 | 521 | 423 | 732 | 691 | 624 | 623 | 518 | 430 |
| 32 | 2.5% KCl | 515 | 470 | 428 | 673 | 650 | 598 | 594 | 546 | 422 |
| 33 | Control | 512 | 487 | 442 | 706 | 680 | 587 | 517 | 434 | 350 |
| 34 | 5.0% KCl | 526 | 521 | 463 | 691 | 713 | 631 | 638 | 645 | 539 |

As can readily be seen, the osmotolerant compressed yeasts maintain their superior leavening activity after storage; their superiority after 4 weeks is particularly notable.

The following examples demonstrate the production of an osmotolerant High Activity Dry Yeast according to the present method.

EXAMPLE 35

Example 3 was repeated, but on a laboratory scale, using 1.25% NaCl and a variant strain of yeast. After the yeast was compressed, it was dried according to conventional methods in an air-lift dryer. On the average, the yields were about 3.5% lower, but the leavening activities were 14% higher in straight dough, 21% higher in lean dough, and 137% higher in straight dough systems over the control, non-osmotolerant yeast. In addition, the activity of the osmotolerant yeast was 133% greater after 21 days storage.

EXAMPLE 36

Example 3 was repeated using a variant strain of a high activity yeast developed by Universal Foods Corporation, Milwaukee, Wisconsin, notable for its high sweet and straight dough activity. Similar results are predicted for any high activity dry yeast strain available in public culture collections that is characterized by relatively high sweet and straight dough activity.

On the average, the yields were about 2.6% lower, but the leavening activities were about 8% higher in straight dough, 13% higher in lean doughs, and 26% higher in sweet dough, over the control, non-osmotolerant yeast. In addition, the activity of the osmotolerant yeast was about 41% higher after 21 days storage.

EXAMPLE 37

Example 34 was repeated, using another variant strain of yeast. On the average, the yields were about 13% lower, and the leavening activities were about 37% higher in straight dough, 31% higher in lean dough, and 51% higher in sweet doughs over the control, non-osmotolerant yeast.

What is claimed is:

1. In a process for producing an osmotolerant baker's yeast by propagating yeast in a series of stages and harvesting yeast from the last stage, the improvement which comprises:
   (a) incrementally feeding nutrient containing water-soluble, ionic, non-nutritive salts to all of the highly aerobic yeast propagative stages except the last stage, said nutrient containing said non-nutritive salts in amounts sufficient to provide a final total ionic concentration of said non-nutritive salts in each of said stages of at least between about 1 and 2% on a weight/volume basis when yeast growth is completed in each of said storage;
   (b) incrementally feeding nutrient containing water-soluble, ionic, non-nutritive salts to the last propagative stage of the yeast produced in the preceding stages wherein the said salt in said nutrient is supplemented with additional non-nutritive, ionizable, water-soluble salt in amounts sufficient to provide a final total ionic concentration of said non-nutritive salts in said last stage of at least 2.5% on a weight/volume basis when the yeast growth in said last stage is complete; and
   (c) harvesting the resulting osmotolerant yeast from the said last stage.

2. A process according to claim 1 wherein the supplementally added non-nutritive, ionizable, water-soluble salt in step (b) is incrementally added to the last stage in an amount of from about 0.3% to about 5% on a weight/volume basis.

3. A process according to claim 1 wherein the non-nutritive, ionizable, water-soluble salt used in the process is selected from the group consisting of NaCl, KCl, $CaCl_2$, $MgSO_4$, $MgCl_2$, $Na_2SO_4$, and $K_2SO_4$.

4. A process according to claim 1 wherein the non-nutritive ionizable, water-soluble salt in step (b) is supplementally added in an amount of from about 0.3% to about 2.5% on a weight/volume basis.

5. A process according to claim 3 wherein the non-nutritive, ionizable salt supplementally added to the last stage is selected from the group consisting of NaCl and $CaCl_2$, and is added incrementally with the nutrient to the last yeast propagation stage in an amount sufficient to achieve a final ionic concentration of at least 2.5% on a weight/volume basis.

6. A process according to claim 1 wherein the supplementally-added, non-nutritive salt is NaCl in an amount from about 0.3% to about 1.25% on a weight/volume basis.

7. A process according to claim 1 wherein the supplementally-added, non-nutritive salt is $CaCl_2$ in an amount from about 0.3% to about 1.25%.

8. A process according to claim 1 wherein the nutrient added is molasses.

9. A process according to claim 1 wherein the supplementally-added ionizable, water-soluble, non-nutrient salt is a calcium salt which is added incrementally to the last yeast propagation stage with the nutrient in an amount sufficient to achieve a final ionic concentration of at least 2.5% on a weight/volume basis.

10. In a process for producing an osmotolerant active dry baker's yeast which includes propagating yeast in a series of stages and harvesting yeast from the last stage and drying the yeast, the improvement which comprises:
    (a) incrementally feeding nutrient containing non-nutritive salts to all of the highly aerobic propagative stages except the last stage, said nutrient containing said non-nutritive salts in amounts sufficient to provide a final total ionic concentration of said non-nutritive salts in each of said stages of at least between about 1 and 2% on a weight/volume basis when yeast growth is completed in each of said stages;
    (b) incrementally feeding nutrient containing water-soluble, ionic, non-nutritive salts to the last aerobic propagative stage of the yeast produced in the preceeding stages, wherein salt in said nutrient is supplemented with additional non-nutritive, ionizable, water-soluble salt in amounts sufficient to provide a final total ionic concentration of said non-nutritive salts in said last stage of at least 2.5% on a weight/volume basis when the yeast growth in said last stage is complete;
    (c) compressing and drying said yeast to produce an osmotolerant, active dry yeast.

11. A process according to claim 10 wherein said non-nutritive salt is selected from the group consisting of sodium, potassium, calcium and magnesium salts.

12. A process according to claim 11 wherein the salts are selected from a group consisting of NaCl, KCl, $CaCl_2$, $MgCl_2$, $Na_2SO_4$ and $K_2SO_4$.

13. A process according to claim 12 wherein said salt is added in amounts of from 0.3% to about 2.5% on a weight/volume basis.

14. A process according to claim 13 wherein said salt is $CaCl_2$ and said addition is made to the last propagative stage.

* * * * *